United States Patent
Totzeck et al.

(10) Patent No.: US 11,499,814 B2
(45) Date of Patent: Nov. 15, 2022

(54) INSPECTION OF BONDING QUALITY OF TRANSPARENT MATERIALS USING OPTICAL COHERENCE TOMOGRAPHY

(71) Applicants: Carl Zeiss Meditec, Inc., Dublin, CA (US); Carl Zeiss AG, Oberkochen (DE); Carl Zeiss Industrial Metrology LLC, Maple Grove, MN (US); Carl Zeiss Meditec AG, Jena (DE)

(72) Inventors: Michael Totzeck, Schwäbisch Gmünd (DE); Marcin B. Bauza, Plymouth, MN (US); Jochen Straub, Pleasanton, CA (US); Muzammil Arain, Milpitas, CA (US); Matthew J. Everett, Livermore, CA (US)

(73) Assignees: CARL ZEISS AG, Oberkochen (DE); CARL ZEISS INDUSTRIAL METROLOGY LLC, Maple Grove, MN (US); CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 15/734,168

(22) PCT Filed: Jun. 12, 2019

(86) PCT No.: PCT/EP2019/065263
§ 371 (c)(1),
(2) Date: Dec. 1, 2020

(87) PCT Pub. No.: WO2019/238715
PCT Pub. Date: Dec. 19, 2019

(65) Prior Publication Data
US 2021/0215470 A1 Jul. 15, 2021

Related U.S. Application Data

(60) Provisional application No. 62/684,508, filed on Jun. 13, 2018.

(51) Int. Cl.
*G01B 11/02* (2006.01)
*G01B 9/02091* (2022.01)
(Continued)

(52) U.S. Cl.
CPC ...... *G01B 9/02091* (2013.01); *G01N 21/8422* (2013.01); *A61B 3/102* (2013.01); *G01N 2021/8438* (2013.01)

(58) Field of Classification Search
CPC .......... G01B 9/02091; G01B 9/0209; G01N 21/8422; G01N 2021/8438; B23K 26/032; B23K 31/125
See application file for complete search history.

(56) References Cited

U.S. PATENT DOCUMENTS

2004/0239946 A1  12/2004 Kane et al.
2007/0291277 A1  12/2007 Everett et al.
(Continued)

FOREIGN PATENT DOCUMENTS

KR  20150102368 A  9/2015

OTHER PUBLICATIONS

De Boer et al., (2017). "Polarization sensitive optical coherence tomography," Biomedical Optics Express 1838, 8(3), 36 pages.
(Continued)

*Primary Examiner* — Tarifur R Chowdhury
*Assistant Examiner* — Jonathon Cook
(74) *Attorney, Agent, or Firm* — Morrison & Foerster LLP

(57) ABSTRACT

An optical coherence tomography (OCT) system (63) is used to inspect bonding points (66A, 66B, 66C) sandwiched between two materials (layers 62, 64 of e.g. displays). The OCT differentiates between a bonding point, e.g. a weld, and air gaps between the two materials. The bonding points are identified as breaks in the air gap between the materials. By (Continued)

extracting various physical characteristics of the bonding points and the gap between the two materials, the present system determines whether the bonding is faulty.

25 Claims, 12 Drawing Sheets

(51) Int. Cl.
    *G01N 21/84*     (2006.01)
    *A61B 3/10*     (2006.01)

(56) References Cited

U.S. PATENT DOCUMENTS

| | | | |
|---|---|---|---|
| 2012/0320380 A1* | 12/2012 | Schonleber | G01B 9/02044 |
| | | | 356/479 |
| 2015/0138564 A1 | 5/2015 | Jung et al. | |
| 2016/0018692 A1 | 1/2016 | Park | |
| 2016/0299527 A1 | 10/2016 | Kwak et al. | |
| 2017/0199405 A1 | 7/2017 | Gupta et al. | |

OTHER PUBLICATIONS

International Search Report and Written Opinion dated Sep. 24, 2019, for PCT Patent Application No. PCT/EP2019/065263, 18 pages.

Wikipedia, "Optical coherence tomography," Available online at <http://en.wikipedia.org/w/index.php?title=Optical coherence tomography&oldid=563952640#Parallel_.28or_full field.29_OCT>, retrieved on Nov. 5, 2014, 14 pages.

\* cited by examiner

INSPECTION OF BONDING QUALITY OF TRANSPARENT MATERIALS USING OPTICAL COHERENCE TOMOGRAPHY

PRIORITY

This application is a National Phase application under 35 U.S.C. § 371 of International Application No. PCT/EP2019/065263, filed Jun. 12, 2019, which claims priority to U.S. Provisional Application Ser. No. 62/684,508, filed Jun. 13, 2018, the contents of which are hereby incorporated by reference in their entirety.

The present invention is generally directed to field of inspecting the bonding of materials transparent to an inspecting light source. More specifically, it is directed to the inspecting of invisible bonding points sandwiched between two transparent material layers of an electronic image display.

BACKGROUND

Image displays are an integral part of many different types of electronic devices. For example, televisions, desktop computers, notebook computers, tablet computers, hand-held computers (e.g., personal digital assistants, PDAs), mobile telephones, wearable electronics (e.g., smart watches), and other specialized electronic devices/tools may include a display for conveying visual information to a user. Such displays may include multiple layers (e.g., a lower substrate layer, multiple intermediate layers, and a top layer), all or some of which may be transparent to the human eye, such as glass layers, for conveying visual information from one layer to another.

Assuring the bonding of these multiple layers may be challenging. Strong bonds are needed since separation between layers may lead to display failure or a degraded image. However, assuring strong bonds may require visible bonding marks, which tend to be unattractive or detract from a viewing experience. Therefore, bonded regions of the layers are often covered by a dark border or bezel. Additionally, some common types of bonds, such as adhesive layers or gluing, may tend to degrade with time so that a housing surrounding the display may be needed to provide additional protection to the display.

It would be desirable to have a strong bonding method that would alleviate the need for a protective housing, and be invisible to a user so as to eliminate the need for covering the bonding area. One promising technology is laser welding of glass, but these welds tend to be invisible or indistinguishable from the surrounding area, which complicates inspection of the welds for defects.

It is an object of the present invention to provide a method of inspecting bonding regions within bonded material layers.

It is a further object of the present invention to provide a method for inspecting invisible welds within layers of transparent materials.

It is a further object of the present invention to provide a bond inspection system suitable for use within a manufacturing line.

SUMMARY OF INVENTION

The above objects are met in a system and method for inspecting the bonding between two materials. The two materials may be dissimilar materials or similar materials, and at least one material may be transparent. The two materials may be bonded by use of laser welding, thermal fusion, gluing, adhesive film, etc. At least some of these bonding methods may result in an invisible, or transparent, bond (e.g., bonding region). For example, the two materials may be transparent glass layers used in the construction of an electronic display, and the bonding region may be invisible and sandwiched between the transparent glass layers. In the case of laser glass welding, a laser may be focused below the junction between the two glass layers, and a weld may grow up from the lower glass layer into the upper glass layer such that a bonding region is formed that expands into both glass layers, with a bonding point at the junction of the two layers. Laser welding of glass is desirable since it produces strong, invisible bonds that facilitate the construction of an electronic display without a bezel. However, since the bonding region is glass, as are the two bonded layers, the bonding region may be substantially invisible within the two bonded layers and thus difficult to inspect for defects.

A physical layer (e.g., air or other material layer) may lay between the two bonded materials, and different layers may create dielectric interfaces. For example, it has been found that due to imperfections at the surface of the two material layers, a gap (e.g., an air gap) may exist between the two layers even after bonding. The present invention may use an optical coherence tomography, OCT, system (e.g., spectral domain point scanning system, swept source point scanning system, or spectral domain line scanning system) to apply a sample beam through a first of the two materials (e.g., the top layer) to reach and acquire scan data of the bonding point sandwiched between the two materials. That is, the OCT may scan an area that includes the bonding region so that the scan includes both the bonding point and non-bonded areas. Because the bonding region (and the bonding point) may be transparent (e.g., made of the same material as the two bonded layers), the OCT may not "see" the bonding point (or bonding region) between the two layers if the bonding area is perfectly homogenous after welding, but it will "see" (e.g., image) the air gap (e.g., a physical layer between the two bonded materials) surrounding the bonding point at the junction between the two layers. It is noted that the OCT system may be optimized for the specular reflection of any dielectric interface. Thus, the OCT may be used to define a physical parameter of the bonding of the two materials based on the scanned data alone, or in combination with other inspection methods, such as visual inspection, reflectometers, ellipsometers, or spectroscopic ellipsometers. The physical parameter may be any metrological property (e.g., measurable property) including at least one of a thickness, refractive index, or birefringence of at least a select one of the two materials and any other physical layer there between. It is noted that birefringence is generally not an inherent material property of glass, but may be induced in glass by stress. Consequently, stressed-induced birefringence in glass may be a marker of high stress regions in glass. It is further noted that the OCT system may be (or may include the functionality of) a polarization sensitive OCT (PS-OCT), which may measure the birefringence properties of the bonded materials (e.g., two glass layers) and/or a weld. For example, the OCT may define the width-span of the bonding point. A lateral scan may produce a bright intensity line corresponding to the air gap between layers, and a dark region corresponding to the undetected, invisible bonding point. The bonding point thus creates a break in the bright intensity line, and the length of this break would correspond to a width-span of the bonding point along the scanning direction. The defined physical parameter may then be used to selectively designate the bonding of the two materials as defective or not defective. For example, a good weld may be defined as having a span-width not smaller than a predefined threshold, or within a predefined width range. Alternatively, if the defined physical parameter is the axial location of the bonding region, then a good weld may be defined as being within a predefined region from the junction of the two layers. Further alternatively, a good bond may be defined as having an air gap not greater than a predefined maximum size air gap. In this case, a smaller air gap may show up as a narrower line in the OCT scan image than a larger air gap. Since a laser glass weld tends to draw the two glass layers closer together within its vicinity, the width (in the axial direction) of a larger air gap may be compared with the width (in the axial direction) of an air gap adjacent a bonding point. A difference greater than a predefined percentage (e.g., greater than 25 percent) may be indicative of a defective bond. The width can be correlated to the brightness measurements by defining a full-width-half-max (FWHM) width of the detected air gap width.

It is noted that the OCT system may be a self-reference system and thus lack (or eliminate the need for) a reference arm. For example, the OCT light source may be split into two light beams and a known relative delay may be introduced between them. The two light beams may then be combined to constitute an OCT beam used for scanning a sample. The OCT is then self-referenced in that a strong reflection from the sample, such as the reflection from the front surface of the glass (e.g., the top surface of the top glass layer), acts as the reference beam, self-interfering with reflections from deeper within the structure, such as a bond region. The relative delay between the two light beams remain constant irrespective of movement in the axial direction so that such movements of the sample do not ill-affect the OCT system. Likewise, the collected light from the sample may be split into two light beams and a known relative delay may be introduced between them. The two light beams may then be combined prior to the detector. The light returning incident on the detector then forms self-interference based on the known delays introduced into the two light beams. In such a design, one would typically choose the relative delay between the two light beams to be similar to the distance between the reference surface and the region of interest to be imaged.

It is noted that the scan depth of the OCT may be expanded by using its complex conjugate component. This, however, may produce a mirror image. In the present case, where the upper and lower boundaries of the two layers form bright lines in an OCT image, the complex conjugate produces phantom lines in the OCT image. In order to determine which image line corresponds to the junction between the two bonded materials, one may use the thickness of one of the two material layers as a reference. For example, the top surface of the top layer is readily identifiable in the OCT image, and by knowing the thickness of the top layer, one may identify a target offset below the top surface of the top layer (e.g., identify an inspection region within a B-scan). The line in the OCT image closest to this offset (or within the defined inspection region) may be identified as corresponding to the junction between the two material layers. Alternatively, since the real and phantom (e.g., complex conjugate) image signals move in phase and out of phase with a delay line, the delay line may be moved to distinguish between real and phantom image signals.

The present system may be implemented in a production line to permit inspection before welding (e.g., determine if the gap is appropriate for welding), inspection after welding, and/or in-process inspection during welding. For example, the OCT system may scan bonded glass layers as they are bonded and proceed down a production line. That is, the OCT system and the two bonded materials may be continuously displaced relative to each other along a first lateral dimension as the OCT system applies its sample beam. For example, the bonded material may be stationary, and the OCT system may move (or scan) across the bonded material. Alternatively, the OCT system may be stationary, and the bonded materials may be transported on a motion stage (e.g. conveyer) past the OCT system, while the OCT system scans across the moving bonded materials in a direction perpendicular to the moving direction of the bonded material (e.g., a first lateral dimension). In this case, the OCT system may also scan in a second direction opposite to the movement of the two bonded materials so as to counter (cancel out) the displacement of the bonded material so that the scan beam defines a scan line perpendicular to a side of the moving bonded materials. The different scanning directions may be achieved by use of one or more scanners within the OCT. The scanner may be one or more of a galvanometer scanner, a MEMS scanner, an electro-optical deflector, and/or a rotating polygon scanner. Optionally, the OCT system may implement a speckle-reduced wiggle scan, as described in U.S. Pub. 20070291277 assigned to the same assignee as the present invention, and herein incorporated in its entirety by reference.

Optionally, the OCT may generate multiple images (e.g., multiple B-scan of the same area), and provide an image for examination by averaging the multiple images. Additionally, the images used for examination may include en face images. Further optionally, the OCT system may be constructed to avoid (e.g., lack) any scanning components. This may be achieved by implementing the OCT system as a spectral domain full field OCT system or swept source full field OCT system.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Embodiments according to the invention are disclosed in the attached claims directed to a method, a storage medium, a system, a device and/or a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts.

DESCRIPTION OF THE PREFERRED EMBODIMENTS

Figure 1:
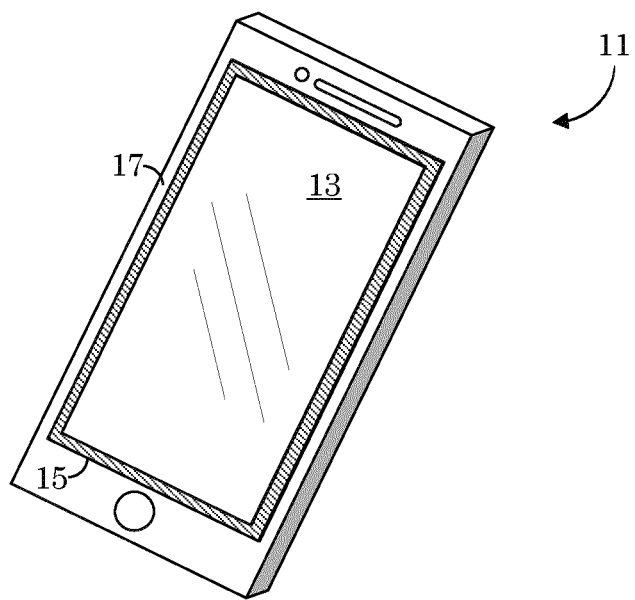
FIG. 1 illustrates a mobile phone having a display (flat screen) with a bezel.

Commercial and consumer grade displays like flat screen TVs, laptops, tablets, or mobile phones may present a glass surface to the user. The manufacturing of these products requires layering and bonding of flat or curved sheets of glass or other materials transparent to vision. These bonds are created either by gluing or by mechanically joining the edges. The mechanical joints may be hidden behind a bezel. Modern designs for computers, tablets, mobile phones, and TVs tend to be "rimless" or are finished with bare glass edges.

Current processes may use glue to bond the glass to the device. The gluing process is generally hard to control and glue might be visible. Therefore, even all-glass front panels typically have a black painted border that hides the glue joint.

Industry is working on alternatives to gluing. One alternative is laser welding. Under well-controlled process conditions, the weld may be virtually invisible to the naked eye, making it a very attractive design for consumer electronics.

Dimensions of laser weld cross-sections may be on the order of 20-50 microns. The problem with "invisible" laser welds is that they are hard to inspect. Surface inspection technology (e.g. ZEISS SurfMax deflectometry) is capable of visualizing the existence of the laser weld, but is not capable of determining whether the weld is located at the correct depth.

The present invention addresses the question of how to inspect bonding points that are located in between (e.g., sandwiched between) two, or more, material layers. For illustration purposes, the present invention is presented as applied to a specific example where one, or more, bonding points are located between transparent layers, and the bonding points themselves may be invisible to a viewer. As explained above, one area where this situation is found is in the construction of electronic displays (e.g., flat panel electronic displays).

Electronic displays are often comprised of multiple, stacked layers, or substrates, each serving a different purpose. For example, a bottom layer may provide structural support, an upper layer may be a polarizer layer, an intermediate layer may provide/support a liquid crystal array or organic light-emitting diode (OLED) array, one or more other layers may provide color filters, still another layer may provide touch sensor circuitry, etc. Since a user is expected to view an image on the display, multiple layers need to be transparent. This complicates a display's construction since the circuitry and other components need to be hidden from the user. Often this requires a bezel, such as darken border and/or a structural housing surrounding a viewing area. Even if one manages to hide the surrounding circuitry, one still has the difficulty of assuring that the display's multiple layers remained bonded to each other since separation of a layer may lead to failure of the display. Because of the need for transparency, glass is often the material of choice for some of the layers that make up a display. Although various transparent glass bonding techniques, such as transparent glue, adhesive films, and thermal fusion have been tried to bond together layers of a display, they have limitations. For example, they may not provide a sufficient level of transparency, or may not provide sufficient structural bonding strength, or their bonding strength may degrade with time.

A promising bonding technique for glass is laser glass welding, but this technique requires high quality control since the resulting bonds are invisible and faulty welds may not be readily apparent. Laser glass welding typically focuses a laser beam slightly below the boundary between two glass layers. This creates a bonding region in the lower glass layer that grows upward toward the upper glass layer. Because of imperfections in the glass surfaces, a small air gap separates the two glass layers, but if the laser is focused at the correct depth with a correct amount of energy, the bonding region will push up to traverse the gap and grow into the upper glass layer. This creates a bonding point at the junction of the two glass layers that bridges the gap between the two glass layers, and a bonding region that penetrates both glass layers. Laser glass welding does not require any additional bonding layer (e.g., adhesive), and the resulting bonding point is made of the same material as the two bonding layers, e.g., transparent glass. Consequently, inspection of the resultant laser welds is not straightforward.

To inspect the laser glass welds (or other bonding points/regions sandwiched between two material layers), an optical coherence tomography (OCT) system is used to scan the junction between the two glass layers, including the bonding points. The OCT system can identify changes in refractivity it encounters during the scanning operation. This permits the OCT to identify the air gap between the glass layers, including the gap surrounding a laser glass weld. In this manner, the present invention can identify various physical qualities of the laser welds, such as determining its cross-sectional size at the junction, breaks in a weld, the size of the gap in its surrounding regions, and non-uniformities; any of which may be used (singularly or in combination) to identify a defective laser glass weld.

In summary, an OCT system is used to inspect bonding points sandwiched between two materials. The OCT differentiates between a bonding point (e.g. a laser weld or the location of glue, an adhesive strip, thermal fusion), and air gaps between the two materials. The bonding points are identified as breaks in the air gap between the materials. Furthermore, if the welding process changes the refractive index of the material and is located far away from the intended location, the air gap will have a step change in the axial direction. If the bonding itself is incomplete, the breaks in the air gap will show a spurious signal, e.g., a signal strength at a break will be lower than that obtained at the air gap. By extracting various physical characteristics of the bonding points and the air gap between the two materials, the present system determines whether the bonding of the two materials is faulty.

As an example of an electronic device, FIG. 1 illustrates a mobile phone 11 having a display (flat screen) 13 with a bezel. The bezel may consist of a darken area 15 and/or a housing 17 that partly covers display 13 and surrounds a viewing region of display 13. Other examples of electronic devices that may use an electronic display, such as display/screen 13, include televisions, desktop computers, notebook computers, tablet computers, hand-held computers (e.g., personal digital assistants, PDAs), wearable electronics (e.g., smart watches), specialized electronic tools, etc. It is to be understood that although display 13 is shown to have a rectangular shape, the display may be configured to have any shape, such as a circle, triangle, hexagonal, etc. As shown, a bezel limits the available viewable area of a display 13, but bezels have traditionally been necessary for providing structural support and protection, plus to hide from a user circuitry and bonding regions of the display 13. Flat displays, like display 13, are comprised of multiple layers of materials that need to be bonded together and secured.

Figure 2:
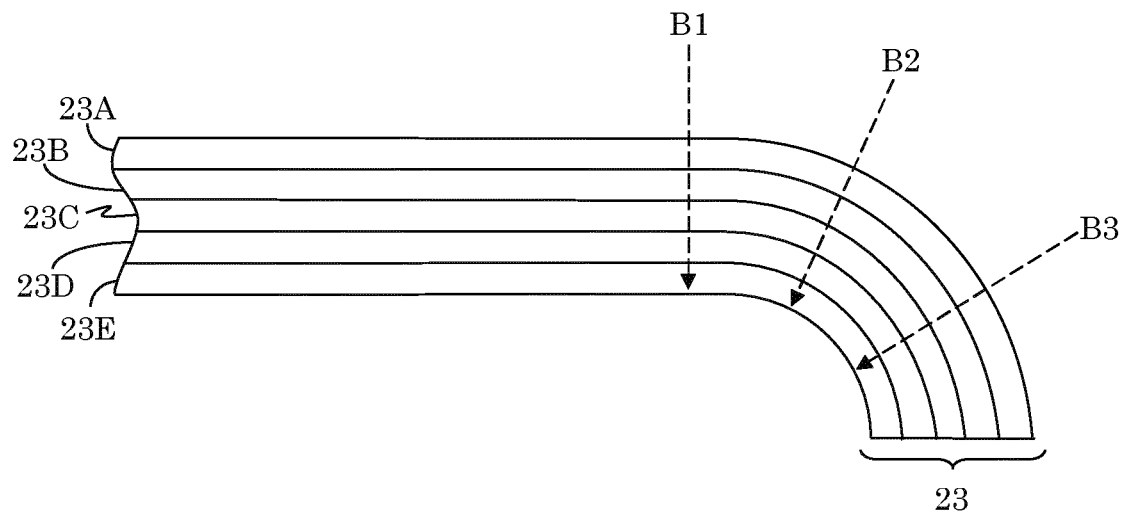
FIG. 2 illustrates sample layers of an electronic display, and sample locations for bonding points.

FIG. 2 illustrates sample layers of an electronic display that may avoid the use of a bezel, and sample exemplary locations B1, B2, and B3 for bonding points. The electronic display may be composed of multiple material layers 23, and in the present example, the display has a curved edged that may extend the viewing area beyond what would traditionally be covered by a bezel. An example of such a display is provide in U.S. Pub. 20160299527 Kwok et al., herein incorporated in its entirety by reference. Bonding locations B1, B2, and B3 may bond any or all of the junctions between the different layers 23. The bonding locations B1, B2, and B3 may be located anywhere on the display, including planar regions and curved regions. Depending upon the arrangement of glass layers to be bonded, bonding locations may be located on any, or all, or a combination of the sides of a device. Periphery circuitry may be hidden at the extreme sides (e.g., beyond the curved area) of the display, so as to avoid the need for a bezel at these sides. Each of the layers may provide a different function for display. For example, layer 23A may be an upper polarizing layer and 23E may be a lower polarizing layer. In the case of a liquid crystal display, inner layer 23C be constitute a liquid crystal layer, and layers 23B and 23D may be substrate layers supporting thin-film transistors, conductive traces, color filter elements, etc. Optionally, touch sensor electronics may be constructed on still other layers. To facility viewing, some of the layers may be transparent substrates, and constructed of different materials, such as clear layers of glass, plastic sapphire or other crystalline materials, transparent ceramic materials, etc. The different layers need to be strongly bonded together. Some typical types of bonding include laser welding, thermal fusion, gluing, adhesive film, etc. In particular, laser welding (e.g., laser glass welding) may provide strong, invisible bonding without the need for any adhesive.

Figure 3:
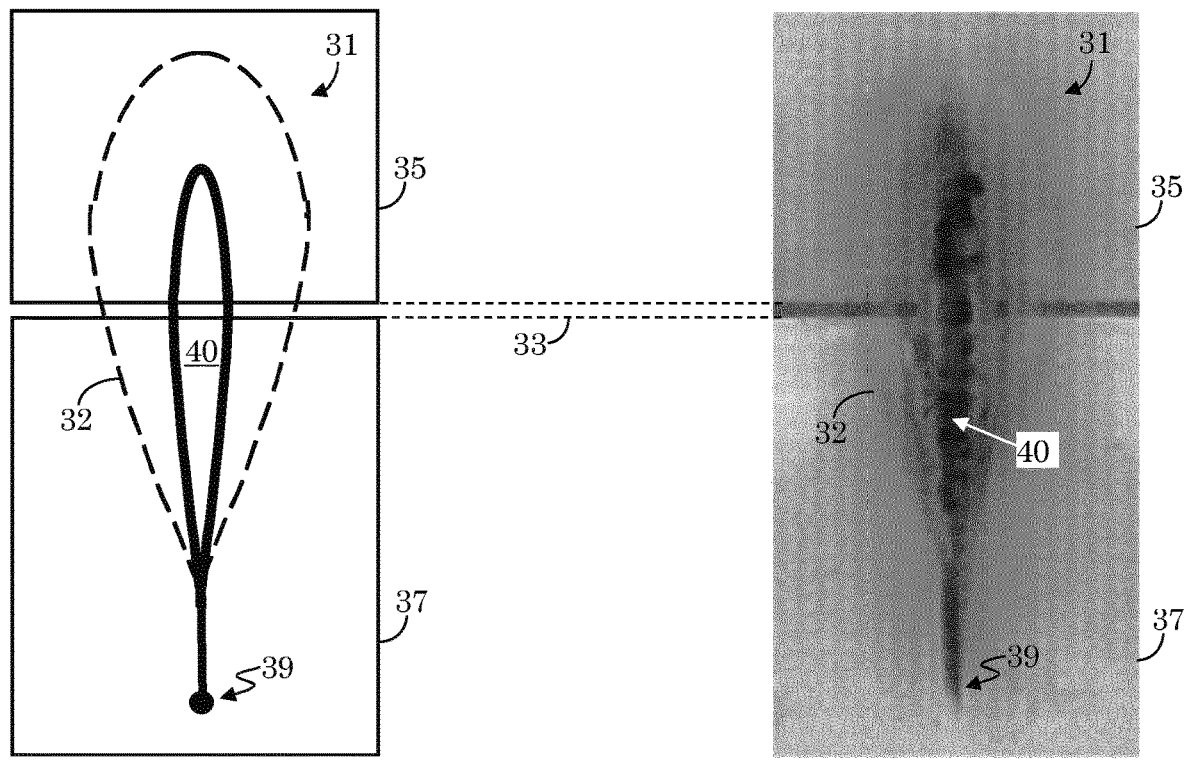
FIG. 3 illustrates a laser glass weld bridging a gap between two glass layers.

FIG. 3 illustrates both a photo and schematic view of a laser glass weld 31 bridging a gap 33 between an upper glass layer 35 and a lower glass layer 37. A laser glass weld may be constructed by applying a laser beam at focal point 39 in the lower of the two glass layers to be welded (e.g., lower glass layer 37). Preferably, the focal point 39 is close to, and below, the gap 33 (e.g., boundary or air gap) between the upper glass layer 35 and lower glass layer 37. This may create a plasma region 40 (e.g., or molten region or bonding region) that grows upward toward the upper glass layer 35. Surrounding the plasma region 32 is what may be termed a heat-affected zone 32, where the glass is heated. Under ordinary conditions, this region will have optical properties which may be a combination of optical properties of glass layer 35 and glass layer 37. If the optical properties of the two glass layers 35 and 37 are sufficiently different or if the welding process produces any anomaly, e.g., reaching the breakdown threshold of the material, it may cause refractive index or optical path length changes for an inspecting beam. With an appropriate laser strength, and a correct focal point location, the plasma region 40 and heat-affected zone 32 may push the upper surface of the lower glass layer 37 upwards to contact and grow into the upper glass layer 35. This creates a successful welding of the upper glass layer 35 and lower glass layer 37. The extent and growth the plasma region 40 and heat-affected zone 32 is dependent upon the strength of the laser. If the focal point 39 is too far below the gap 33, the plasma region may not bridge the gap 33 and the two glass layers 35/37 may not be welded successfully. If the focal point is too close to the junction, the weld junction may be too thin to provide adjudicate bonding strength. Additionally, if the laser power is not sufficient, the plasma region may not bridge the gap 33 and the two glass layers 35/37. It is noted that as two glass layers 35/37 are welded together, they are drawn closer together so that the gap 33 is lessened, at least in regions peripheral to the laser weld (e.g., the bonding point). As illustrated, the laser weld may generally have an inverted tear drop shape such that for a given laser power (which may determine the diameter of a plasma region and heat-affected zone region), a relationship (or correlation) may be made between the diameter of the laser weld and the location of the focal point. Thus, one may determine an offset of the laser weld (or focal point) in the axial direction (z-direction) relative to the gap between the glass layers 35/37. However, since the present laser weld is generally invisible and made of the same material as the two layers being bonded together (e.g., glass), it has heretofore been difficult to inspect such welds for defects such that one might not depend solely on a laser glass weld to bond multiple glass layers to construct a bezel-free display. For example, U.S. Pub. 20170199405 to Gupta applies laser glass welding to a side profile of a display, but relies on adhesives for bonding an upper layer to a lower layer of the display, and thus does not achieve a bezel-free display.

In order to assure reliable laser glass welding, one needs a method for inspecting such welds in production. In some embodiments, the present invention monitor the quality of laser glass welds indirectly by observing the air gap surrounding a laser glass weld between an upper glass layer and a lower glass weld.

Figure 4A:
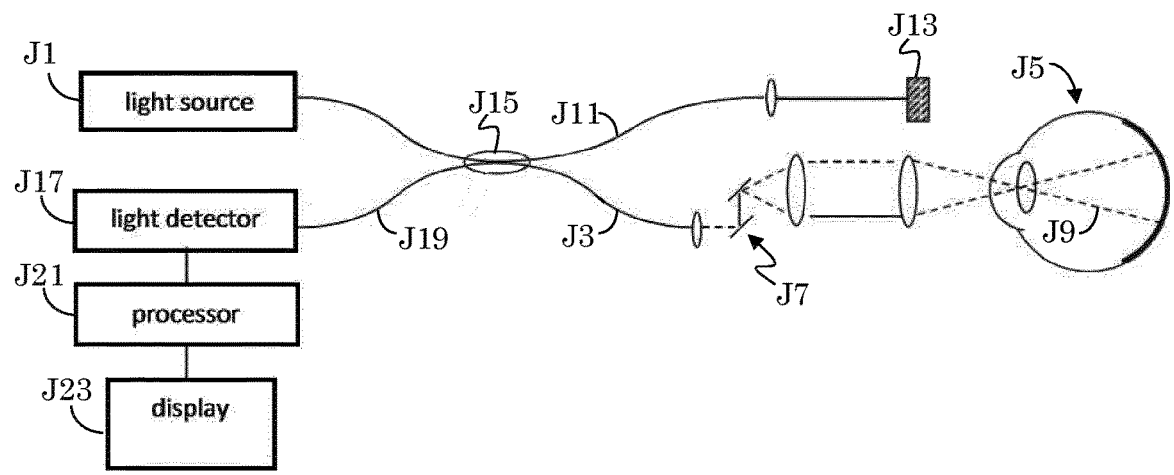
FIG. 4A illustrates an example of an optical coherence tomography (OCT) system.

FIG. 4A illustrates an example of an optical coherence tomography (OCT) system, which may be used to provide an OCTA image. For ease of illustration, the present OCT system is illustrated as imaging an eye, but it is to be understood that the present OCT system (or variations on the present OCT system) may be used to image other samples, such as bonded material layers used in the construction of a flat panel display. Light from a light source J1 is routed, typically by optical fiber J3 down a sample arm to illuminate a sample J5, such as tissues in a human eye or other test sample. The light source J1 may be a broadband light source with short temporal coherence length in the case of spectral domain OCT (SD-OCT) or a wavelength tunable laser source in the case of swept source OCT (SS-OCT). The light is scanned, typically with a scanner J7 between the output of the fiber J3 and the sample J5, so that the beam of light (dashed line J7) is scanned laterally (e.g., in x and/or y directions) over the area or volume to be imaged. Light scattered from the sample J5 is collected, typically into the same fiber J3 used to route the light for sample illumination. Reference light derived from the same light source J1 travels a separate path (e.g., a reference arm), in this case involving optic fiber J11 and retro-reflector J13 with an adjustable optical delay. Those skilled in the art will recognize that a transmissive reference path can also be used and that the adjustable delay may be placed in the sample or reference arm of the interferometer. Collected sample light is combined with reference light, typically in a fiber coupler J15, to form light interference in a detector J17. Although a single fiber port J19 is shown going to the detector J17, those skilled in the art will recognize that various designs of interferometers may be used for balanced or unbalanced detection of the interference signal. The output from the detector J17 is supplied to a processor (e.g., computing device/system) J21. The results may be stored in the processor J21 and/or displayed on a display J23. The processing and storing functions may be localized within the OCT system, or instrument, or functions may be performed on an external processing unit to which the collected data may be transferred. This external processing unit may be dedicated to data processing or perform other tasks which are quite general and not dedicated to the OCT device. The processor J21 may contain, for example, a field-programmable gate array (FPGA), a digital signal processor (DSP), an application specific integrated circuit (ASIC), one or more general purpose graphic processing unit (GPGPU), a system-on-chip (SoC), or a combination thereof.

The sample and reference arms in the interferometer may consist of bulk-optics, fiber-optics, or hybrid bulk-optic systems and may have different architectures such as Michelson, Mach-Zehnder or common-path based designs as would be known to those skilled in the art. Light beam as used herein may be any carefully directed light path. In time-domain systems, the reference arm may have a tunable optical delay to generate interference. Balanced detection systems are typically used in time domain OCT (TD-OCT) and SS-OCT systems, while spectrometers are used at the detection port for SD-OCT systems. The invention described herein may be applied to other types of OCT systems, such as spot scanning, multi-spot scanning, partial field and full field imaging systems, or speckle-reduced wiggle scan (e.g., as described in U.S. Pub. 20070291277, herein incorporated in its entirety by reference).

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram, results in a complex valued OCT signal output $Aj(z)=|Aj|e^{i\varphi}$. The absolute value of this complex OCT signal, $|Aj|$, reveals the profile of scattering amplitudes (or intensities) at different path lengths, and therefore scattering as a function of depth (z-direction) in the sample. Similarly, the phase $\varphi j$ may also be extracted from the complex valued OCT signal. The profile of scattering as a function of depth is called an axial scan (A scan), and it may refer to a pixel point on an image. A set of A-scans measured at neighboring locations in the sample produces a cross-sectional image (tomogram or B-scan) of the sample, and may be termed a fast scan (e.g., lateral or transverse scan). A collection of B-scans collected at different transverse locations on the sample makes up a data volume or cube (e.g., sometimes termed a slow scan). For a particular volume of data, the term fast axis may refer to the scan direction along a single B-scan whereas slow axis may refer to the axis along which multiple B-scans are collected. A frontal image, as viewed along the axial direction (Z-direction) may be termed an en face image, and it may be constructed by averaging volume data along the axial direction. Additionally, multiple scans of the same regions of a sample may be averaged together to provide a clearer image of a structure. A variety of ways to create B-scans are known in the art including but not limited to along the horizontal or x-direction, along the vertical or y-direction, along the diagonal of x and y, or in a circular or spiral pattern. B-scans may be in the x-z dimensions but may be any cross-sectional image that includes the z-dimension.

Figure 5:
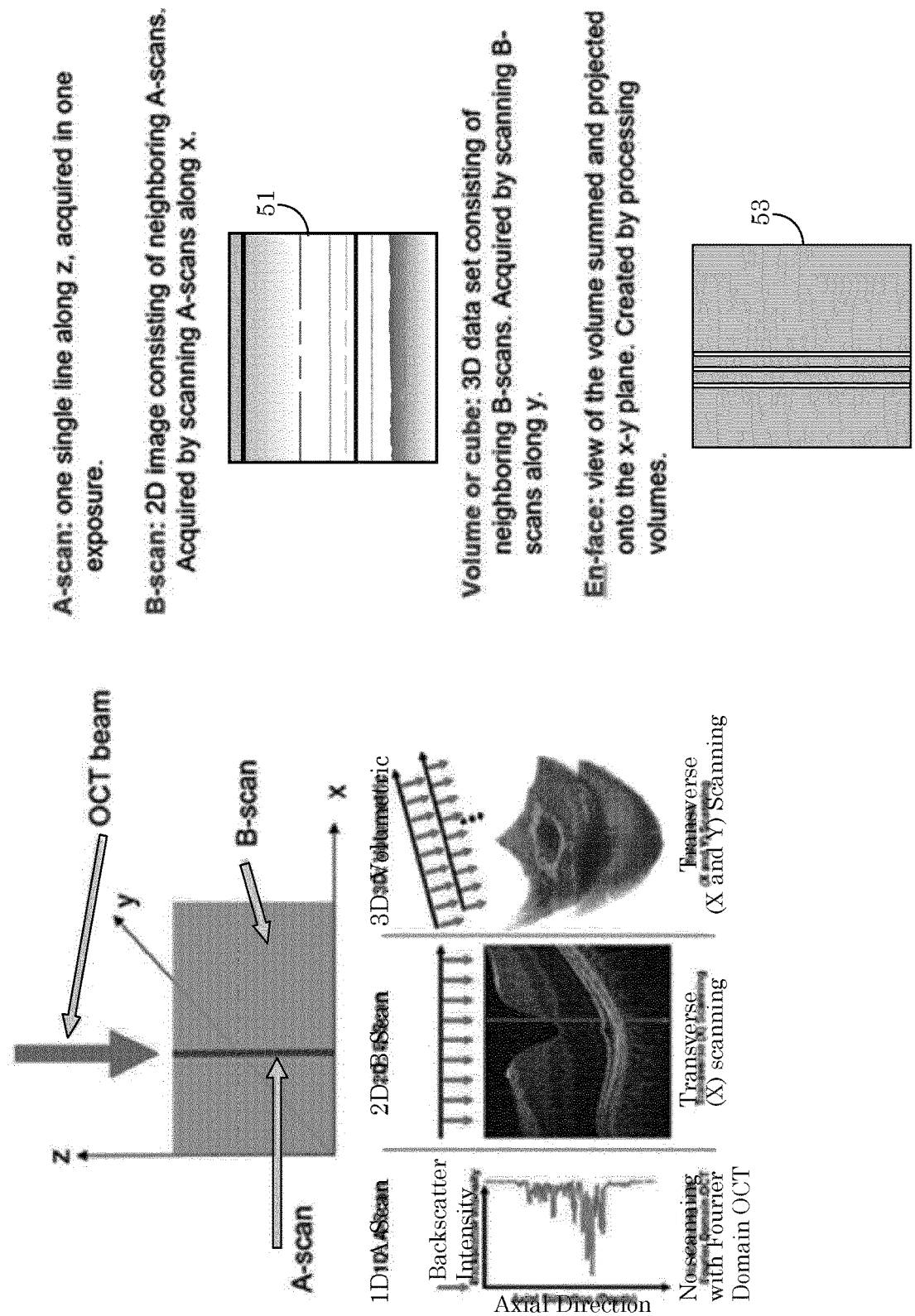
FIG. 5 illustrates the operation of an OCT system and sample images created by an OCT system.

FIG. 5 illustrates the operation of an OCT system and provides sample images that may be created by an OCT system. An OCT beam is applied axially in the z-direction to define a single A-scan. This may be termed a one-dimensional (1D) scan, or A-scan. As explained above, returning backscatter is combined with a reference signal from a reference arm to extract axial location information. Multiple A-scans may be taken next to each other in a transverse scan (e.g. the OCT beam is scanned in the X-direction) to define a two-dimensional (2D) scan, or B-scan. This creates a 2D slice image of a test subject. An example of a B-scan of laser glass welding 51 is shown. Multiple B-scans may be taken next to each other to create a three-dimensional (3D or volumetric) scan, which may be termed a volume or cube. This may be achieved by scanning in both the X-axis and Y-axis directions. By projecting a volume onto the X-Y plane, one may define a frontal view, or en face view, of a test subject. An en face image of laser glass welding 53 is shown.

In some embodiments, a customized OCT system may be used to image transparent layer samples after they have been laser welded at an internal surface interface. The present invention may evaluate the presence or absence of a weld, as well as the lateral size of the weld inside the material (e.g., in between the two layers). This method enables visual and automated inspection of a laser weld or thermal fusion inside a transparent medium.

Figure 6:
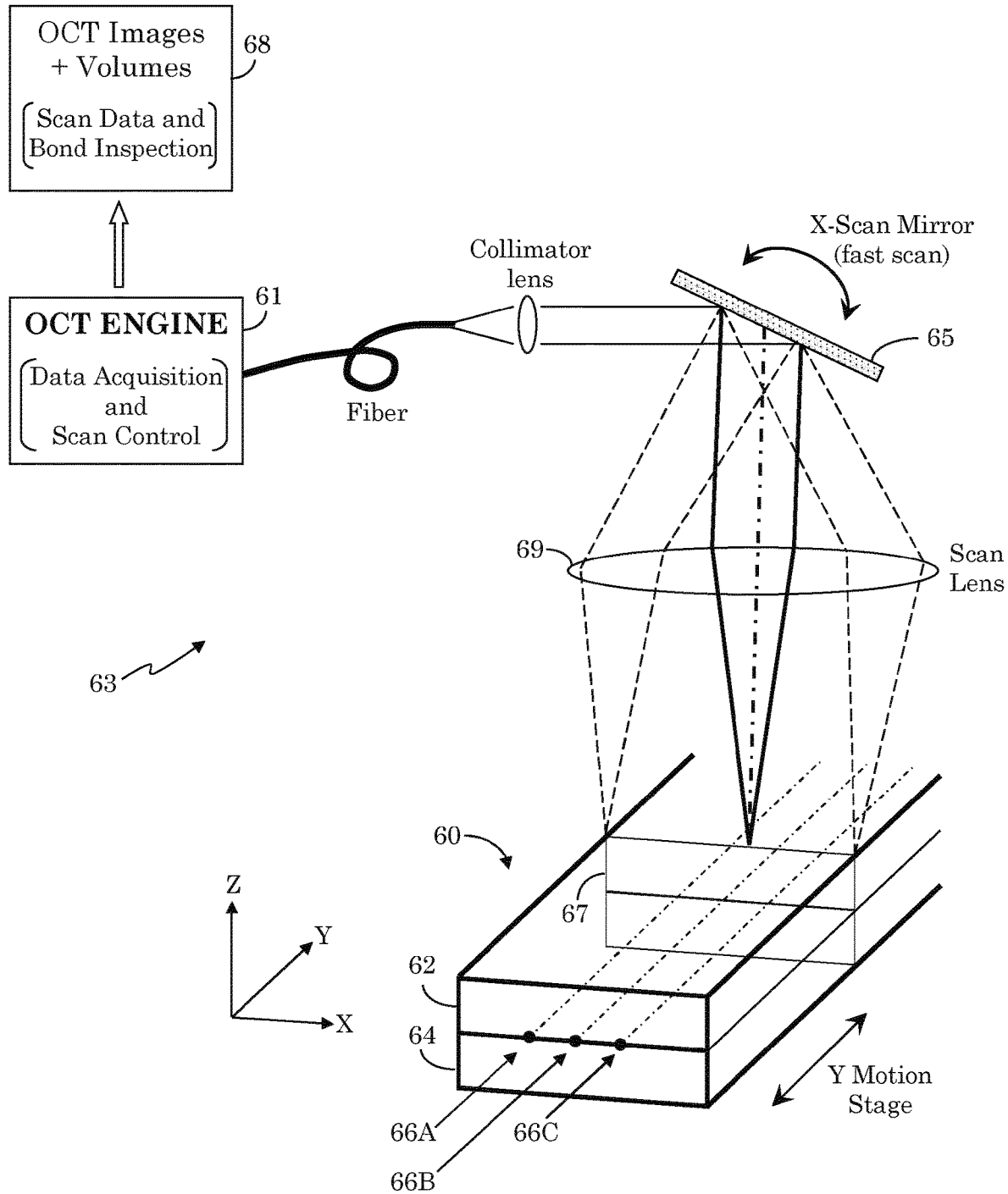
FIG. 6 illustrates a setup for using an OCT system to inspect the bonding of two materials.

FIG. 6 illustrates a setup for using an OCT system 63 to inspect the bonding of a multi-layer sample 60 (e.g., two material layers with a layer of air (or other physical layer) there between), in accord with the present invention. An OCT engine 61 provides data acquisition and scan control. For example, the OCT engine 61 may incorporate the light source J1, light detector J17, processor J21, fiber coupler J15, and reference arm of the OCT system of FIG. 4A. The OCT engine 61 applies a sample beam (e.g. OCT beam) via an optic fiber and a collimator lens to a scanner 65. In the present example, scanner 65 scans the OCT beam along the X-axis through a scan lens 69 so as to create B-scans 67 along the X-Z plane. The OCT system 63 may be optimized for the specular reflection of any dielectric interface between layers. The OCT beam scans a multi-layer sample 60 (e.g. two or more layers), but in the present example, multi-layer sample 60 is shown to consist of two bonded material layers (an upper layer 62 and a lower layer 64) with an air gap (e.g. an additional physical layer) there between, and three rows of bonding points (e.g., laser welds) 66A, 66B, and 66C sandwiched between upper layer 62 and lower layer 64. Laser welds 66A, 66B, and 66C may be created in a dotted and/or dashed pattern, and although they are illustratively shown arranged linearly, they may be arranged in any free form pattern at a single site or at a plurality of sites. The OCT engine 61 scans multi-layer sample 60 as the sample 60 is continuously moving along the Y-axis direction. For example, a motion stage (e.g., conveyer) may provide this motion. Alternatively, multi-layer sample 60 may be stationary while the OCT system is moved relative to the sample 60. Further alternatively, the OCT system may provide a second scanner to scan along the Y-axis (e.g., see scanner J7 of the OCT system of FIG. 4A) so as to counter the Y-axis motion of multi-layer sample 60. In this manner, the X-scanner may capture B-scans that are truly perpendicular to a side wall of multi-layer sample 60 as if the sample 60 were stationary relative to the OCT system. OCT engine 61 may process the scan data to provide OCT Images 68 and provide bond inspection, as explained more fully below.

The OCT system 63 may define/determine one or more physical parameters of the two bonded materials and any other physical layer there between, as explained more fully below. The physical parameter may be determined based upon the scanned data alone, or in combination with other inspection methods, such as visual inspection, reflectometers, deflectometers, ellipsometers, or spectroscopic ellipsometers. Visual inspection may be used to determine any obvious degradation of the glass, e.g., formation or newton rings to indicate air gaps or contamination. A reflectometer may be used to determine the refractive index and or thickness map of the sample based upon the complex reflection of the sample. An ellipsometer may be used to determine the polarization properties map including refractive index and thickness map of the sample. A spectroscopic ellipsometer may be used to determine the polarization properties map including refractive index and thickness map of the sample as a function of wavelength, and may determine these parameters more precisely than other methods.

Alternatively, the functions of OCT system 63 may be expanded. For example, OCT system 63 may incorporate material specific contrast, which may be used to directly differentiate between different materials (e.g., tissues). That is, the present OCT may exploit additional properties of light besides intensity. For example, the present OCT may incorporate the function of a polarization sensitive OCT (PS-OCT) and take advantage of the fact that some materials and tissues may change a light's polarization state, and thereby add an additional contrast channel and provide quantitative information. OCT system 63 may incorporate the functionality of a PS-OCT by incorporating some additional components, which may be incorporated into OCT engine 61, where appropriate.

Figure 4B:
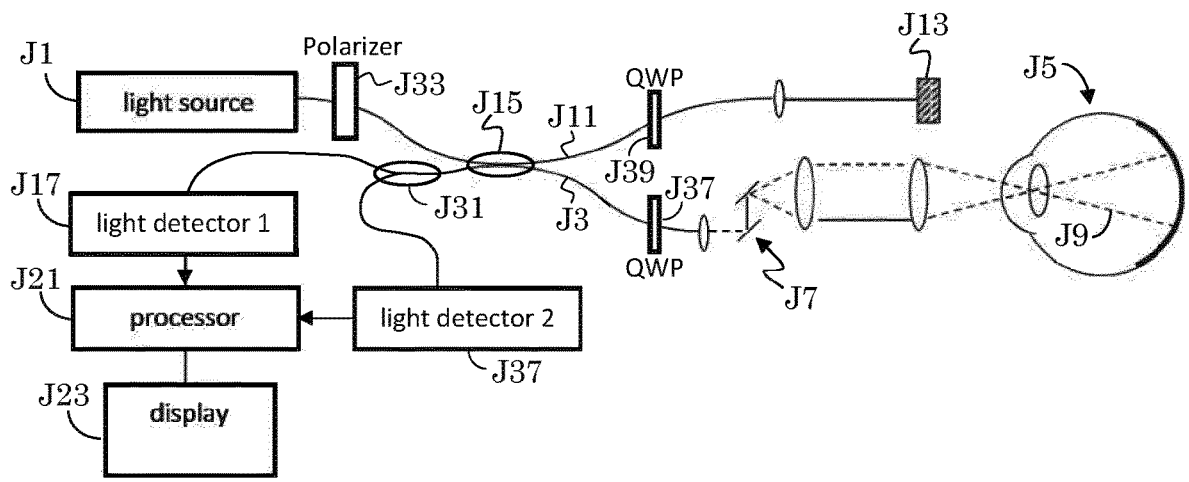
FIG. 4B illustrates an example configuration of components added to the OCT system of FIG. 4A to incorporate the function of a polarization sensitive OCT (PS-OCT).

FIG. 4B illustrates an example configuration of components added to the OCT system of FIG. 4A to incorporate the function of a polarization sensitive OCT (PS-OCT). All elements similar to those of FIG. 4A have similar reference characters and are described above. It is to be understood that any and all of these added components may be selectively, functionally removed (or circumvented or deactivated), as appropriate, to achieve a particular OCT function, as would be understood by one versed in the art. A polarization controller (not shown) may be added to the light source J1, a polarizer J33 may also be added to the light source J1. A first quarter wave plate (QWP) J39 may be added to the reference arm and a second QWP J37 may be added to the signal arm. A polarization beam splitter J31 may be placed after the light has interfered and before any detector to separate the beam into two orthogonal polarization states. Duplicate detector J17 and J37 may then detect both orthogonal polarization states. Processor J21 may then process the information to extract Jones matrix elements. A fuller description of PS-OCT may be found in "Polarization sensitive optical coherence tomography—a review [Invited]", by De Boer, Hitzenberger and Yasuno, *Biomedical Optics Express* 1838, Vol. 8, No. 3, 1 Mar. 2017, which is herein incorporated in its entirety by reference. A PS-OCT uses information that is carried by polarized light to extract additional information about materials, which may help to better differentiate among different materials. An example of using PS-OCT to examine the bonding of materials may be to determine the birefringence of the sample. This information might not be available using simple OCT system alone. This information can further be used to determine the stress induced before and after the welding process. This can further be used to inspect the deterioration of the weld as it ages. Birefringence is a material property of crystals, but not glass. However, birefringence may be induced in glass by stress to form so-called "stressed-induced birefringence." This stressed-induced birefringence in glass may be used as a marker for high stress regions in glass. For example, if cracks are to form in the glass (e.g., glass weld), one may expect these cracks to form at high stress regions, which may be identified by birefringence. In this manner, inspection for birefringence in glass provides an immediate advantage of indicating locations that may be more susceptible to cracks, or other damage.

Figure 4C:
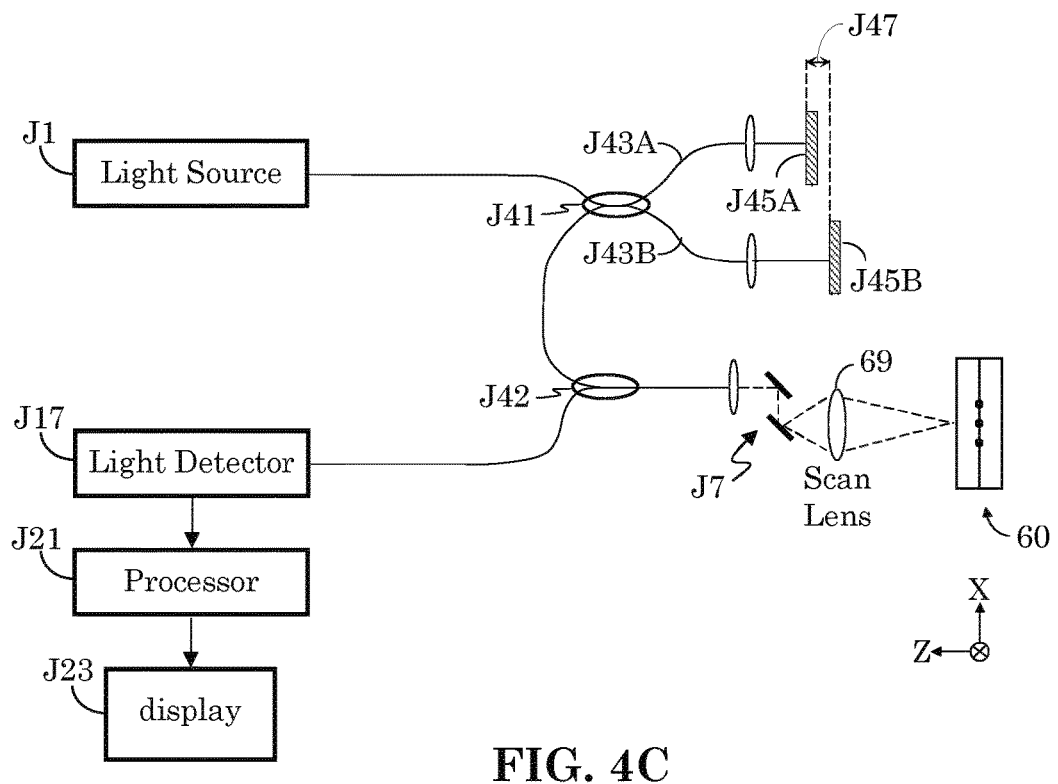
FIG. 4C illustrates an alternate OCT system suitable for use in the setup of FIG. 6 for inspecting material bonding, and which eliminates the need for a reference arm.

FIG. 4C illustrates an alternate OCT system suitable for use in the setup of FIG. 6 for inspecting material bonding. All elements similar to those of FIGS. 4A, 4B and 6 have similar reference characters and are described above. The OCT configuration of FIG. 4C eliminates the need for a reference arm, such as optic fiber J11 and retro-reflector J13 of FIGS. 4A and 4B. In the present configuration, light from light source J1 is routed through light coupler J41 along at least two delay paths J43A and J43B to respective retro-reflectors (e.g., mirrors) J45A and J45B, each providing a different delay to achieve a self-referencing configuration. A distance offset (separation) J47 between retro-reflector J45A and J45B is known, and preferably made similar to region of interest to be imaged, e.g., similar to the distance between front surface of sample 60 and bond region between the two glass layers. Consequently, the delay introduced by each retro-reflector relative to the other is likewise known. The two returned, differently delayed, signals from paths J43A and J45B are combined at fiber coupler J41 and routed through a second fiber coupler J42 though scanner J7 to the sample to be imaged 60. In the present case, the sample to be image is shown as the multi-layer sample 60 of FIG. 6, and the scanner is shown as the X-Y scanner J7 of FIGS. 4A and 4B. The scatter signals returning from multi-layer sample 60 are passed through fiber coupler J42 to light detector J17, where they form an interferogram due to self-interference based on the different delays introduced by paths J43A and J43B. In this manner the captured light is self-referenced, and no separate reference arm is needed. Furthermore, since the relative delay between the two signals from paths J43A and J45B remain constant irrespective of movement in the axial direction, the performance of the OCT system is not ill-affected by axial movement of sample 60. Processor J21 may then convert the interferogram into a spectrum for further analysis, as explained above.

Thus, OCT system 63 determines metrological properties (e.g., measurable properties) including at least one of a thickness, refractive index, or birefringence of at least a select one of the two materials and any other physical layer there between.

Figure 7B:
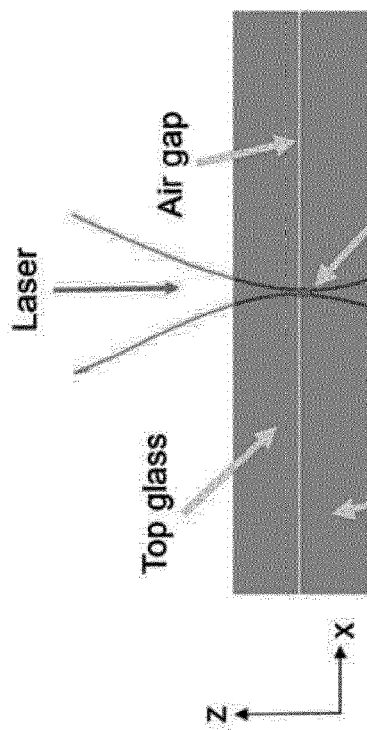
FIG. 7B illustrates the laser glass welding of the two glass layers of FIG. 7A.
Figure 7D:
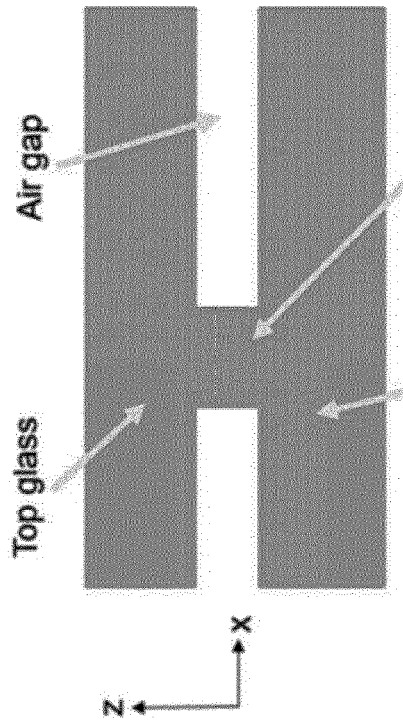
FIG. 7D is an idealized, close up view of the laser weld of FIG. 7C.
Figure 7A:
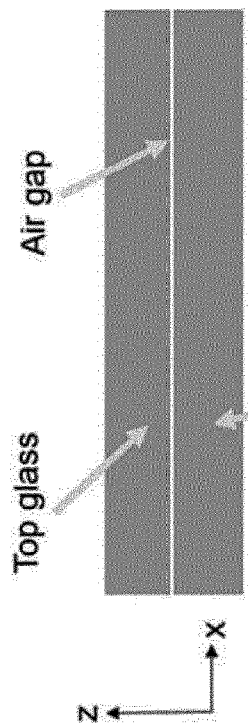
FIG. 7A illustrates two glass layers to be laser glass welded.
Figure 7C:
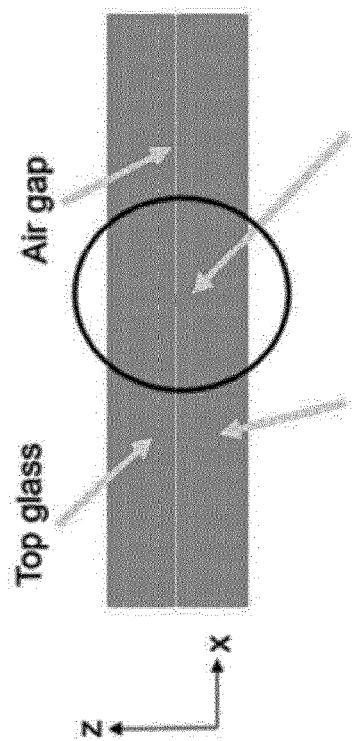
FIG. 7C illustrates the glass layers of FIG. 7A bonded by a laser weld.

FIGS. 7A to 7D illustrate a laser welding process. In FIG. 7A, two glass samples are placed together, but a small air gap remains between them. Optionally, a vacuum or clamp may be used to reduce the size of the gap between them prior to laser welding. FIG. 7B illustrates the laser glass welding of the two glass layers of FIG. 7A. A laser is focused and melts the glass surface of both pieces (e.g., the top glass and bottom glass). The weld is inside the sample (e.g., bridges the gap between the upper glass and lower glass). Once the laser is turned off, the glass cools down, hardens, and bonds, resulting in a laser weld, as illustrated in FIG. 7C. FIG. 7D is an idealized, close up view of the laser weld of FIG. 7C. The weld is of the same material as the two glass pieces and therefore completely transparent. If the two glass pieces are different, the resultant welding location may contain slightly different refractive index properties.

Figure 8:
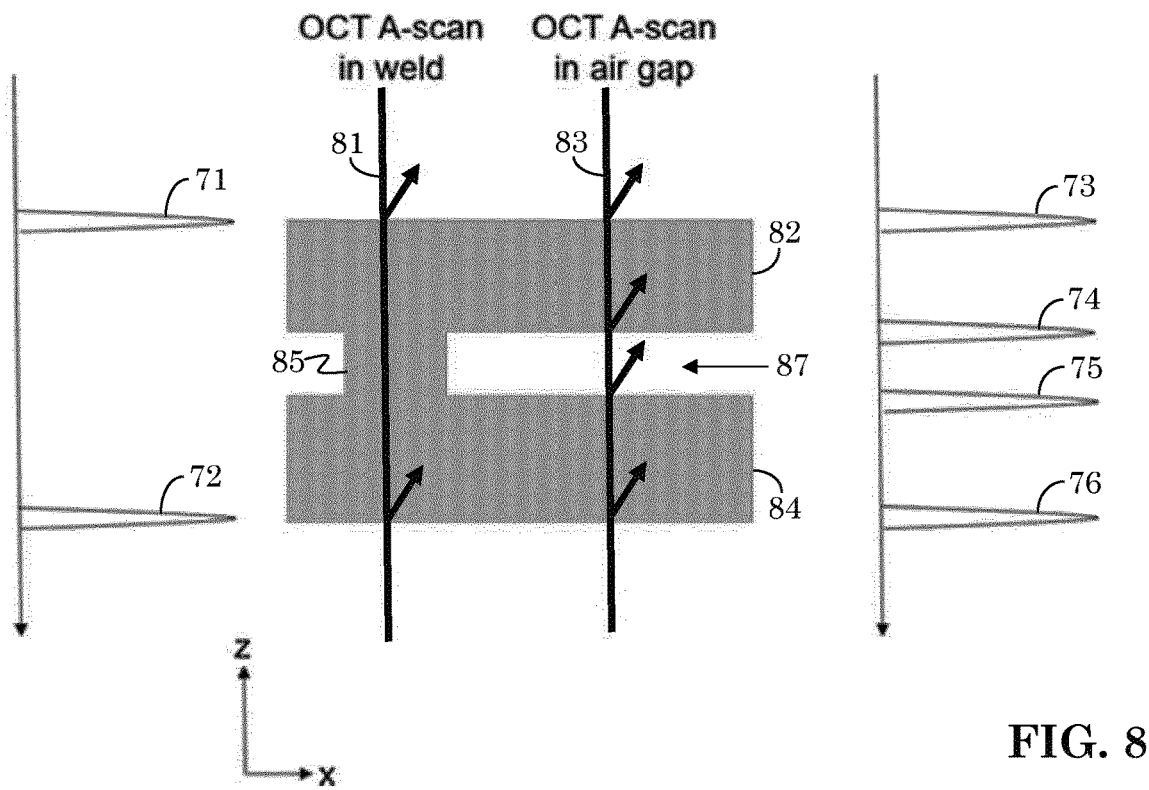
FIG. 8 illustrates two OCT A-scans of two bonded glass layers, one A-Scan at a laser weld, and another at an air gap position.

FIG. 8 illustrates two OCT A-scans of two bonded glass layers 82/84, one A-Scan 81 is located at a laser weld 85, and another A-scan 83 is located at an air gap position 87. OCT is sensitive to scattered and specular reflections. The glass pieces (or layers) 82/84 and the laser weld 85 are of high optical quality and homogeneity and are not scattering. Therefore, OCT signals are acquired from specular reflections at air/glass interfaces. A single A-scan 81 applied perpendicular to the top glass 82 surface and propagated through the weld 85 would therefore detect two signals, 71/72, one signal 71 at the top surface of the top glass 82 and one signal 72 at the bottom surface of the bottom glass 84. A single A-scan 83 through an area that has not been welded will in return detect four signals 73, 74, 75 and 76 at the top and bottom air-glass boundaries of each glass layer 82/84, as shown. Scanning the A-scan across (e.g., transversely) in x-direction results in a B-scan, which represents a cross section of the welded area.

Figure 9:
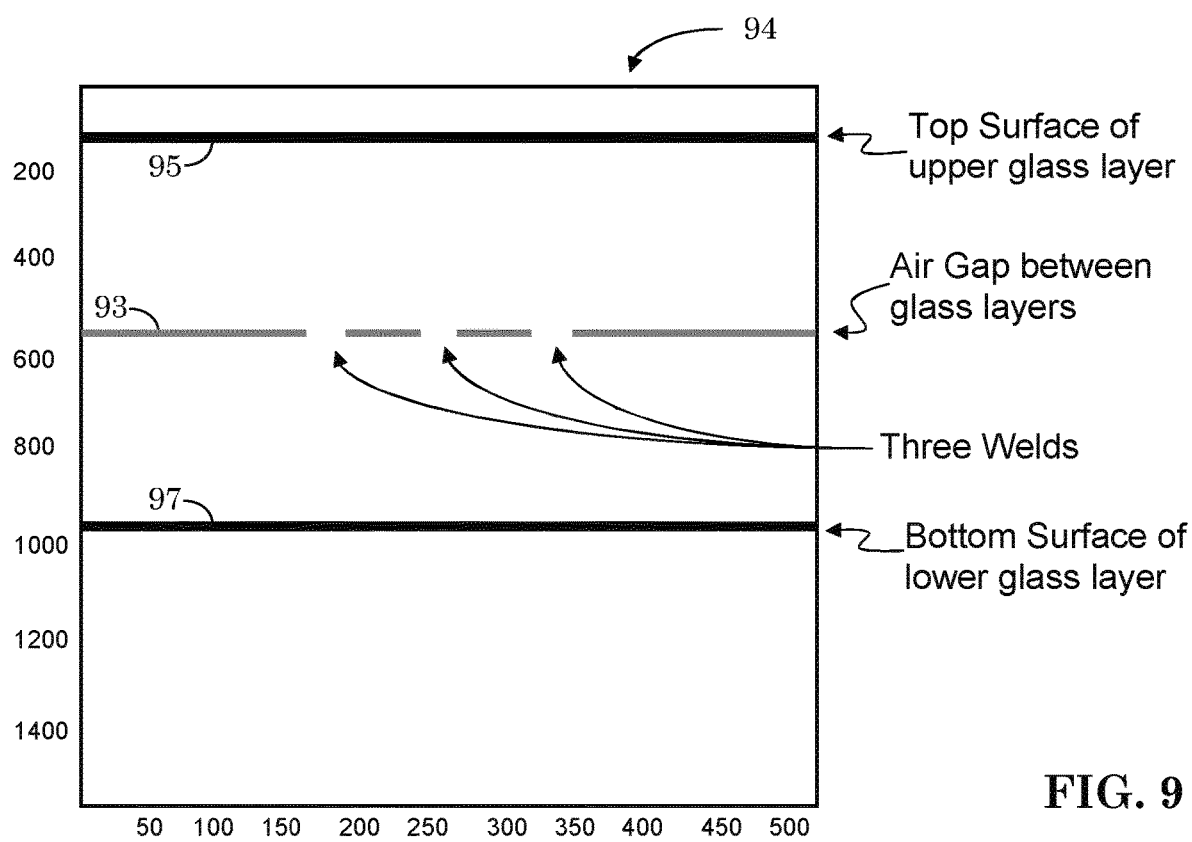
FIG. 9 illustrates negative view of an exemplary OCT B-scan of two bonded glass layers with three laser welds.

FIG. 9 illustrates negative view of an exemplary OCT B-scan 94 of two bonded glass layers with three laser welds. Typically in a black-and-white image, the regions shown in FIG. 9 as dark would be light to indicate a strong scattering signal, but for ease of viewing, a negative view of a typical black-and-white image is provided. Using the method described above, the OCT system can detect the presence and absence, and the width of laser welds as illustrated in the B-scan 94. Line 93 indicates the interface (e.g., gap) between the two bonded glass layers. As shown, line 93 is broken by three blank regions (low or no signal regions). These blank regions correspond to where three welds are placed in parallel to bond the two glass layers (e.g., two microscope slides or other structures having glass-to-glass bonding). The signal at the air gap 93 is substantially lower than the signal 95 at the top surface and the signal 97 at the bottom surface because the air gap is limited by surface roughness of the two inner glass surfaces. The resulting occasional contact between both slides reduces the overall signal strength. From the variation of the signal strength the OCT system can infer on the homogeneity of the mechanical contact between the two slides. A break in homogeneity, for example an increase in signal strength of greater than 25%, may indicate a faulty weld.

Figure 10:
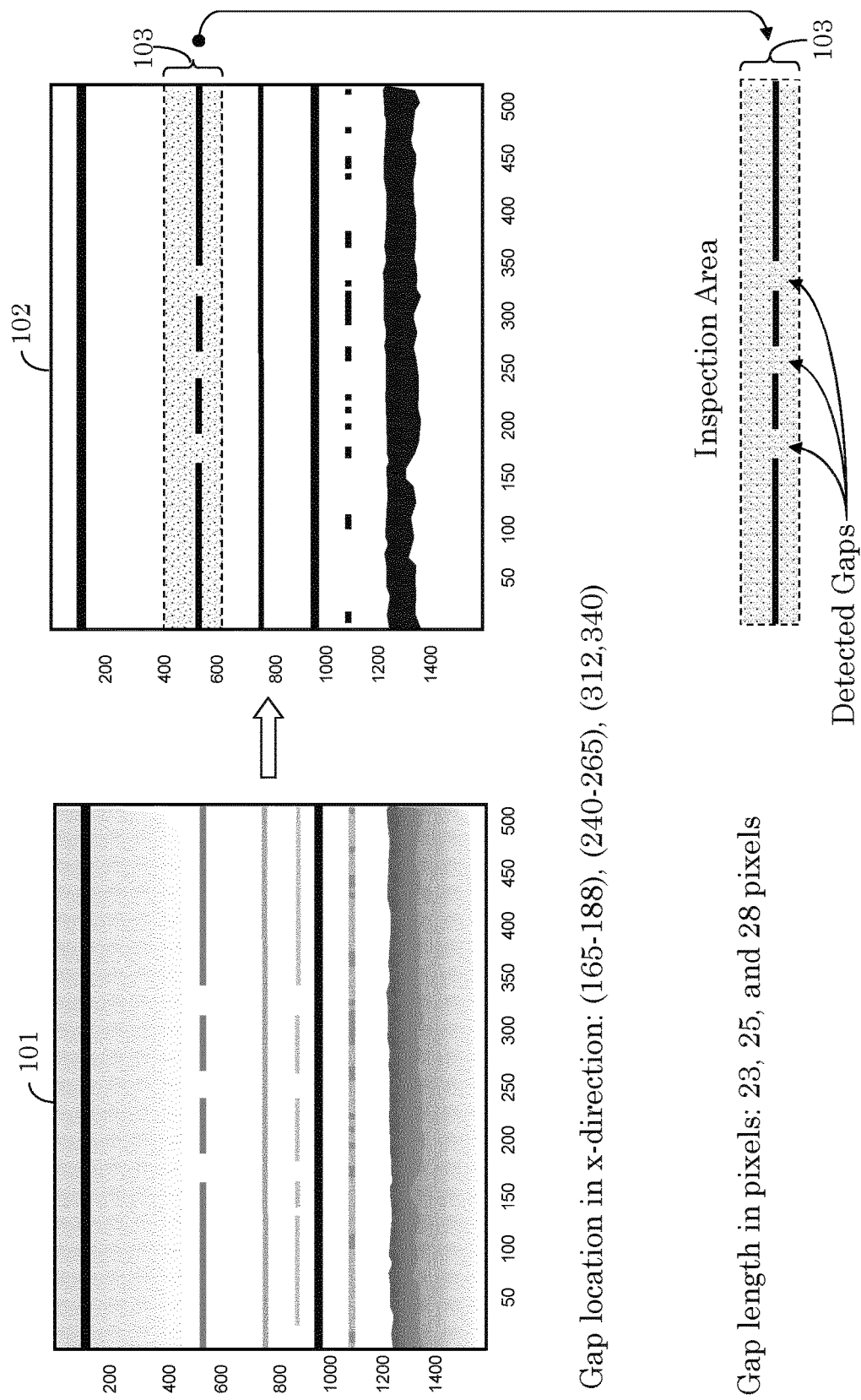
FIG. 10 illustrates a process for extracting OCT scan data related to laser glass welds.

Various image enhancements, image processing, and automatic detection techniques of the width of a weld may be incorporated into the present process. FIG. 10 illustrates an enhanced process for extracting OCT scan data related to laser glass welds. B-scan 101 shows multiple lines (both true lines and phantom lines due to reflection images, such as caused by the complex conjugate in the operation of the OCT system, e.g., resulting from application of the Fourier transform). Optionally, one may binarize B-scan 101 to produce B-scan 102. To identify the true line that correspond to the boundary between the two layers, one may identify an inspection area 103 in which the target true line is expected to reside. As stated above, the strongest signal lines are likely to correspond to the upper surface of the upper layer and to the lower surface of the lower layer. Thus, one may determine the inspection area 103 from a known depth (thickness) of the upper layer and/or lower layer. The inspection area 103 may then be extracted, as shown, for closer examination. This inspection area may also be mapped to the original B-scan 101. In the present example, the X-coordinates may correspond to A-scan positions and be correlated to units of length. In this manner, the width-span of a weld along the B-scan may be detected. The transverse (lateral) resolution is preferably smaller than the intended width detection. In the present example, the lateral coordinates of the three detected welds (corresponding to the detected gaps) are (165-188), (240-265), and (312-340). Determination of a good weld may be made from a reference weld known to be good (e.g., a so-called "golden weld"). Various physical characteristics may be extracted from the golden weld, and parameters for detecting a faulty weld may constructed therefrom. Parameters that are deemed more important to a good weld may be weighted more heavily in the differentiating for a good weld from a faulty weld.

Figure 11:
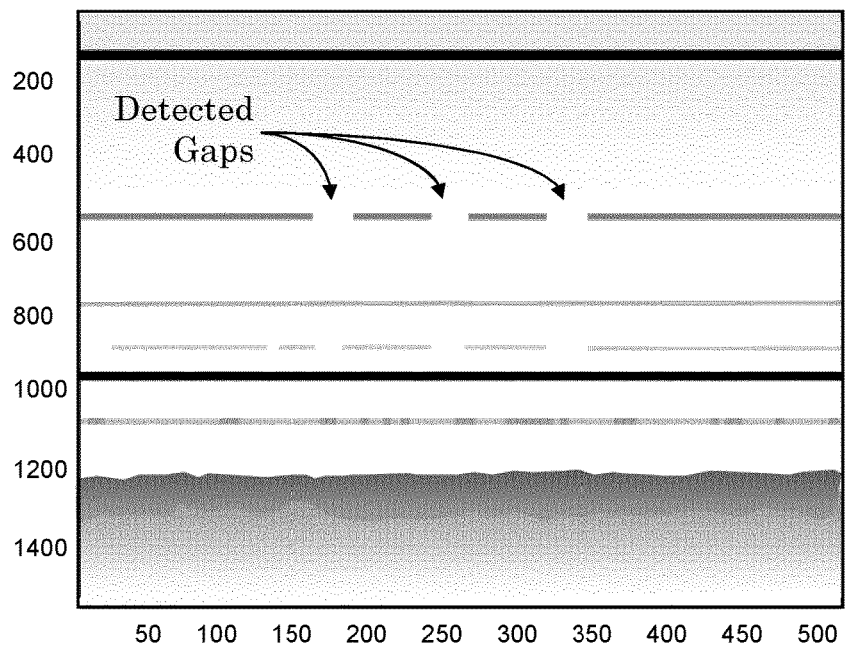
FIG. 11 illustrates an OCT B-scan of laser glass welds.

FIG. 11 illustrates another OCT B-scan of laser glass welds. The observed width of a detected gap may be used to determine if the weld is off from a target position (e.g., if the laser focal point is not at an expected depth). As explained above (e.g., with reference to FIG. 3), this may be determined by establishing a correlation between weld width at the junction of two layers and the focal point of the laser glass weld. This may be done by examining golden welds as reference. The present setup may be incorporated into an existing manufacturing line to provide automated detection and examination (e.g., determine proper position and size of) the welds, such as for assuring they are aligned.

The above examples use transparent glass samples, but the present method may also be applied to other transparent material (e.g., transparent to the OCT beam), where transparency is defined relative to the OCT wavelength-range, i.e. with this method the OCT system can inspect bonding or welding inside materials that transmit the OCT wavelength. For example, the present system may inspect welds of non-transparent plastic at appropriate wavelengths, e.g., to permit the OCT beam to pass through the plastic.

If the dispersion properties of the weld are determined, one may select an OCT system with a suitable wavelength where direct viewing of welds may also be possible. For example, the scattering property of a material may be modified by being melted and cooled. By knowing the scattering property of a laser glass weld, and assuming that they are different from its surrounding medium (e.g. non-welded glass) a frequency for the OCT beam may be selected that will respond to the laser weld and not to the glass layers. This would create a 3D image of the laser glass weld within the bonded material.

Additionally since the Z direction in OCT depends upon the optical path length, i.e., product of distance times the refractive index material, any abnormality in the refractive index of the material will show up as a discontinuity in the next air-sample interface. This situation can arise especially if the two materials being welded together have different optical properties making the resulting welded region optical properties different than the surrounding region, thus enabling direct viewing of weld region possible through the OCT system.

The method can further be used to measure the thickness of the samples before and after the weld. This could detect any bulging or dips in the welded samples caused by a faulty welding process. This method can further detect defects in the sample like bad boundaries, contamination, incomplete welds, and damage spots. Additionally, the contrast, signal-to-noise ratio (SNR), and image quality of the B-scan may be increased by: a) Averaging; b) Speckle reduction using "wiggle scan" (per US20070291277A1); c) Avoiding the etalon effect by tilting the samples; and d) Avoiding the etalon effect by tilting the incident beam using the y scanner.

En face images created by the OCT system may also be used to gain additional information about the weld abnormalities when combined with visual inspection or with B-scan data or independently. Generating en face images over a given 2-D area aids in the detection any contamination on the glass. The en face image may be created as a continuous image by applying relative motion between sensor and sample. As explained above, the sample may be moved with a moving Y-motion stage, or the OCT sensor may be moved relative to the sample. En face images may further be created by scanning in X and Y directions using the scanners in the scan head of the OCT system. Using the en face analysis enhances the determination and quantification of welded area. An en face image can also be used to ensure that the OCT beam is perpendicular to the direction of motion of the glass material thus aiding in determining a perfect alignment of the OCT beam.

Figure 12:
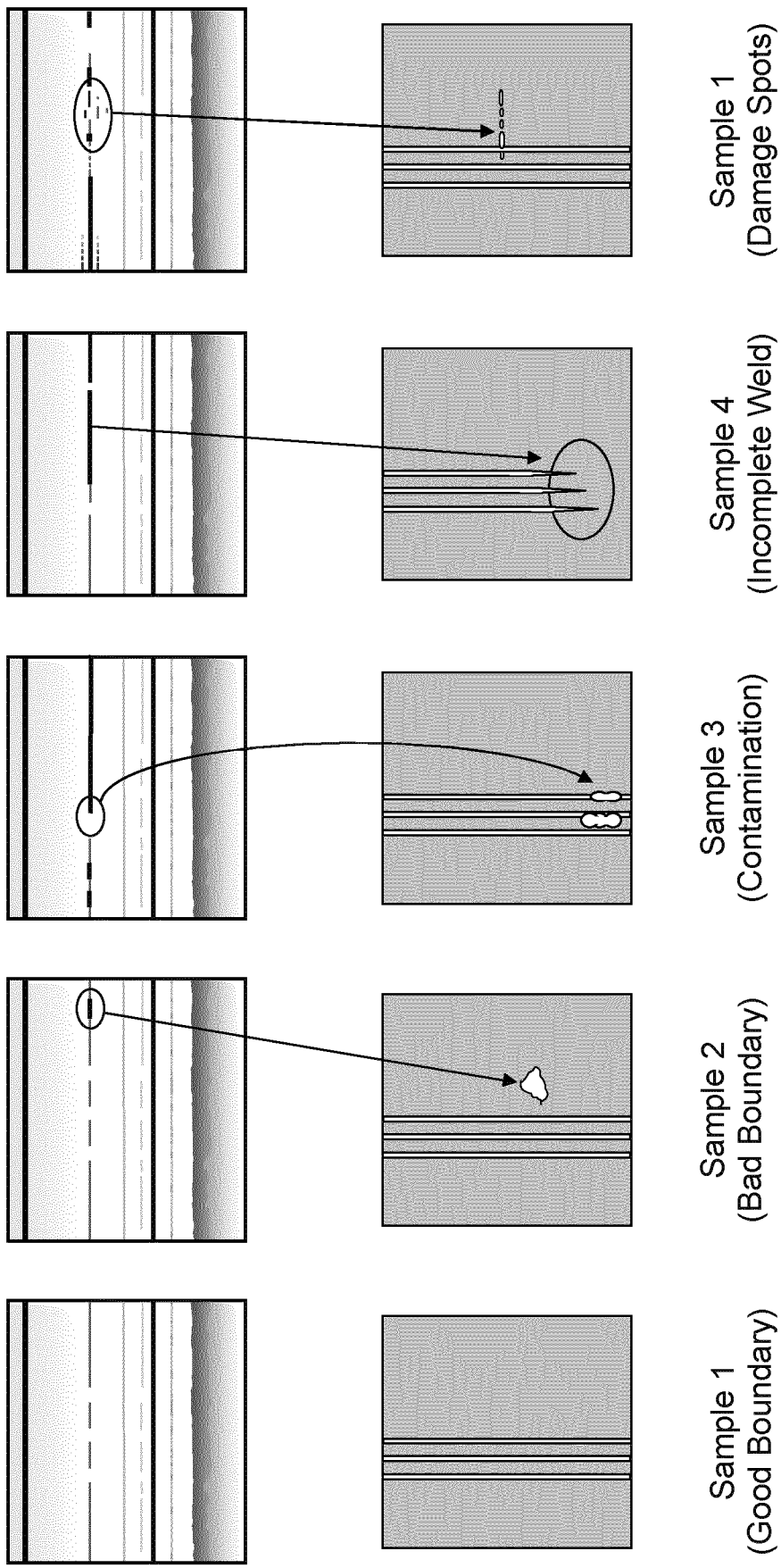
FIG. 12 illustrates the examination of laser welds using a combination of OCT B-scans and corresponding en face images to identify various conditions of laser glass welds.

FIG. 12 illustrates the examination of laser welds using a combination of OCT B-scans (top row) and corresponding en face images (bottom row) to identify various conditions of laser glass welds. Sample 1 illustrates a good laser weld. Sample 2 illustrate a fault due to a bad boundary. This shows up in the bright spots in (e.g., breaks in the homogeneity of) the boundary line in the B-scan, and as interruptions in the laser weld in the welding pattern in the corresponding en face image. Sample 3 is an example of contamination between the two glass layers. In its B-scan, this is shown as a long bright line indicating a relatively large separation between the layers. As explained above, a good weld would typically reduce the separation between layers. The contamination is also visible in the corresponding en face image. Sample 4 illustrates an incomplete weld. This specific fault is more evident in the en face image where the break in welding is visible. However, the B-scan also identifies the break in homogeneity of the boundary line, which is an indicator of a faulty weld. Sample 5 show an example of damage spots in a weld. The B-scan shows this as multiple breaks smaller than a desired width along with intermittent bright spots. The damage is also evident in the corresponding en face image. This is also a case where the weld has changed the optical properties of the material significantly such that the boundaries are not continuous.

Figure 13:
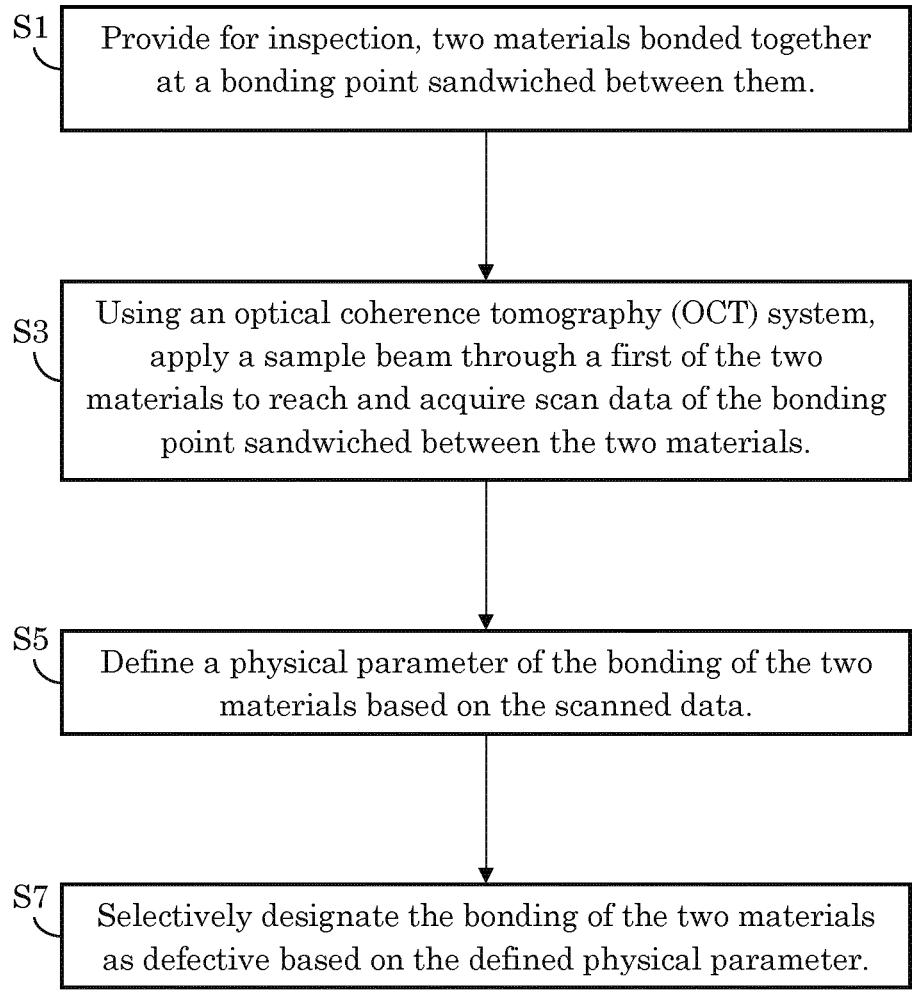
FIG. 13 illustrates an example method for inspecting the bonding of two materials.

FIG. 13 illustrates an example method for inspecting the bonding of two materials. The method may begin at step S1, where two (or more) bonded material are provided (e.g., accessed) for inspection. The two materials may be bonded by at least one bonding point sandwiched between them. The two materials may be, for example, transparent glass layers, and the bonding point may be defined by a laser glass weld. At step S3, an optical coherence tomography (OCT) system is used to apply a sample beam through a first of the two materials (e.g., through the top glass layer) to reach and acquire scan data of the bonding point sandwiched between the two materials. As described above, the sample beam may penetrate both material layers, so as to observe an air gap between them. At step S5, at least one physical parameter of the bonding of the two materials is defined based on the scanned data. For example, the scan data may be used to determine the width-span of the laser weld at the junction of the two material layers, or to identify breaks in the laser weld, or air gaps greater than a maximum distance, or non-uniformity (e.g., abrupt changes) in the size of the air gap, especially near a laser glass weld. At step S7, the bonding of the two materials is selectively designated as defective based on the defined physical parameter. For example, if the width of a scanned laser weld is not lay within a predefined range, the laser weld may be designated as defective. Similarly, if the air gap near a glass weld is larger than a predefined maximum, the weld may be designated as defective. Otherwise, the laser weld may be designated as not defective.

Although this disclosure describes and illustrates particular steps of the method of FIG. 13 as occurring in a particular order, this disclosure contemplates any suitable steps of the method of FIG. 13 occurring in any suitable order.

Figure 14:
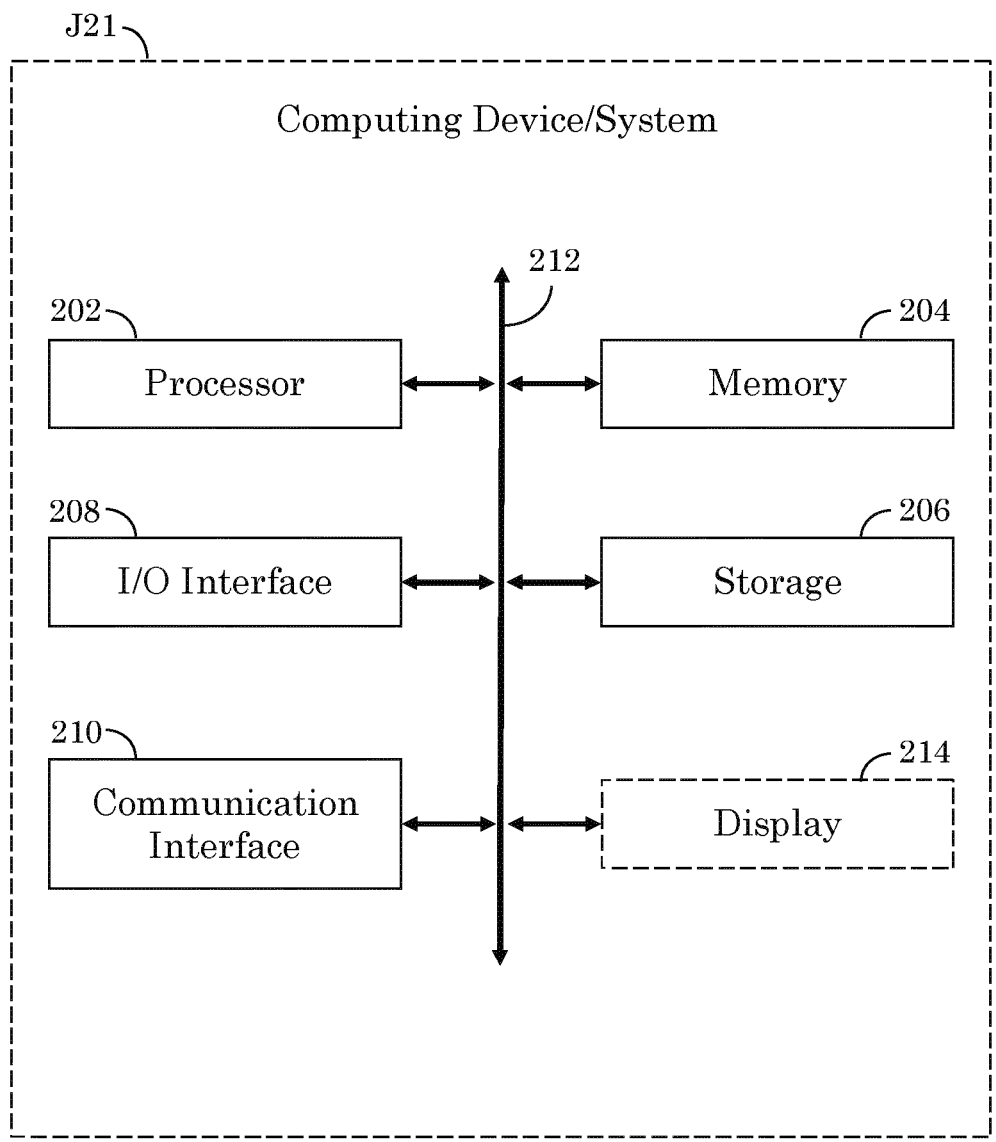
FIG. 14 illustrates an example computer device (or computer system).

FIG. 14 illustrates an example computer device (or computer system), e.g., J21 of FIGS. 4A, 4B, and 4C. In some embodiments, one or more computer systems may perform one or more steps of the methods of FIG. 13. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, or a combination of two or more of these. Where appropriate, the computer system may reside in a cloud, which may include one or more cloud components in one or more networks.

In some embodiments, the computer system includes a processor 202, memory 204, storage 206, an input/output (I/O) interface 208, a communication interface 210, and a bus 212. The computer system may optionally also include a display 214, such as a computer monitor or screen. Processor 202 includes hardware for executing instructions, such as those making up a computer program. For example, processor 202 may be a central processing unit (CPU) or a general-purpose computing on graphics processing unit (GPGPU). Memory 204 may include main memory for storing instructions for processor 202 to execute or to hold interim data during processing. For example, memory 204 may include random access memory (RAM), such as dynamic RAM (DRAM) or static RAM (SRAM). In some embodiments, storage 206 may include long-term or mass storage for data or instructions. For example, storage 206 may include a disk drive (HDD or SSD), flash memory, ROM, EPROM, or other type of nonvolatile memory. I/O interface 208 may include one or more interfaces for communication with I/O devices, which may enable communication with a person (e.g., user). Communication interface 210 may provide network interfaces for communication with other systems or networks. For example, communication interface 210 may include a network interface controller (NIC) and/or a wireless NIC for communication with another computer system on a network. Communication interface 210 may further include a Bluetooth interface or other type of packet-based communication. Bus 212 may provide a communication link between the above-mentioned components of the computing system.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. A method for inspecting a bonding of two materials using an optical coherence tomography (OCT) system generating a sample beam of radiation, the two materials being glass and laser bonded together at a bonding point sandwiched between them wherein the laser bond is transparent to the sample beam, wherein there are air gaps between the two materials proximate to the bonding point, the method comprising:
applying the sample beam through a first of the two materials and into at least a portion of the second material to reach and acquire scan data associated with the bonding point and proximate air gaps sandwiched between the two materials; and
selectively designating the bonding of the two materials as defective based on the scanned data.

2. The method of claim 1, further including:
defining a metrological property of the bonding of the two materials based on the scan data, the metrological property including at least one of a thickness, refractive index, and birefringence of at least a select one of the two materials and any other physical layer therebetween;
wherein the designating of the bonding of the two materials as defective is further based on the defined metrological property.

3. The method of claim 1, further including:
defining a measure of a width-span of the bonding point at the junction between the two materials based on the scan data;
wherein the designating of the bonding of the two materials as defective is based at least in part on the measure of the width-span.

4. The method of claim 1, wherein the bonding point is part of a bonding region extending into the two materials, the method further including:
defining an axial offset of the bonding region relative to a junction between the two materials based on the scan data, the designating of the bonding of the two materials as defective being based at least in part on the defined axial offset.

5. The method of claim 4, wherein the axial offset is determined based on a predefined correlation between axial offset and width-span of the bonding point at the junction between the two materials.

6. The method of claim 1, wherein the scan data of the bonding point is acquired as part of scanning the sample beam across a region of the junction between the two materials including the bonding point, the method further comprising:
defining an image of the junction between the two materials based on the scanning of the sample beam across the region of the junction, a relative gap size in the junction between the two materials corresponding to a relative intensity in the defined image;
comparing a relative intensity of a first region of the junction adjacent to the bonding point with a second region of the junction distant from the bonding point; and
designating the bonding of the two materials as defective in response to the intensity of the second region being a predetermined percentage greater than the intensity of the first region.

7. The method of claim 1, wherein the sample beam is further applied through the two materials and laterally scanned across the two materials, the method further comprising:
defining a two-dimensional, cross-sectional image of the two materials based on the lateral scan across the two materials, the cross-sectional image providing a plurality of imaged lines including true boundary lines of the two materials and phantom boundary lines of the two materials, the phantom boundary lines resulting from a complex conjugate image component and being offset from the true boundary lines; and
identifying as the junction between the two materials the imaged line closest to an axial location having a predefined offset from an outer boundary of a selected one of the two materials, the predefined offset being a thickness of the selected one of the two materials.

8. The method of claim 1, wherein:
the bonding point is part of a bonding region that extends into the two materials, the bonding region having a light dispersion property different from either of the two materials;
a wavelength of the sample beam is selected based on the light dispersion property of the bounding region to differentiate the bounding region from the two materials; and
the sample beam penetrates the bonding region and provides axial information of the bonding region; and
the method further including, defining a three-dimensional image of the bonding region within the two materials.

9. The method of claim 1, wherein the OCT system is one of a spectral domain point scanning system, a swept source point scanning system, a spectral domain line scanning system, a swept source line scanning system, a full field spectral domain, or a full field swept source system.

10. The method of claim 1, wherein the OCT system and the two bonded materials are continuously displaced relative to each other along a first lateral dimension as the OCT system applies the sample beam.

11. The method of claim 10, wherein the OCT system scans the sample beam in first direction traversing the first lateral dimension and in a second direction opposite to the relative continuous displacement between the OCT system and the two bonded materials so as to counter the relative continuous displacement.

12. The method of claim 1, wherein the OCT system includes at least one of a galvanometer scanner, a MEMS scanner, an electro-optical deflector, and a rotating polygon scanner.

13. The method of claim 1, wherein the scan data is obtained by use of a speckle-reduced wiggle scan.

14. The method of claim 1, wherein:
the scan data includes repeated scans of the bonding point; and
the method further including, generating multiple images from the repeated scans of the bonding point, and averaging the multiple images.

15. The method of claim 1, further including defining an en face image, the designating of the bonding of the two materials as defective being based at least in part on the en face image.

16. The method of claim 1, wherein the two bonded materials are parts of an electronic image display.

17. The method of claim 1, wherein the OCT system lacks any scanning components and is one of a spectral domain full field OCT system or a swept source full field OCT system.

18. The method of claim 1, wherein the OCT system is optimized for the specular reflection of any dielectric interface.

19. The method of claim 1, wherein:
the two materials are bonded by a welding process;
the OCT system is a PS-OCT system;
the PS-OCT system measures birefringence properties of the two materials and the bonding point before, during, and after the welding process; and
the bonding of the two materials is further designated as defective based on the measured birefringence properties.

20. The method of claim 1, wherein the OCT system has a light source and introduces known delays to at least two light beams from its light source, the at least two light beams being combined to constitute the OCT beam.

21. The method of claim 1, further including:
defining a metrological property of the bonding of the two materials using the OCT system and at least one other inspection method, including visual inspection, reflectometers, deflectometers, ellipsometers, or spectroscopic ellipsometers, the metrological property including at least one of a thickness, refractive index, and birefringence of at least a select one of the two materials and any other physical layer there between;
wherein the designating of the bonding of the two materials as defective is at least in part based on the defined metrological property.

22. The method of claim 1, wherein the OCT system is self-referenced and lacks a separate reference arm.

23. A method for inspecting a bonding of two materials, the two materials being bonded together at a bonding point sandwiched between them and wherein the bonding point is part of a bonding region extending between the two materials, the method comprising:
using an optical coherence tomography (OCT) system, applying a sample beam through a first of the two materials to reach and acquire scan data of the bonding point sandwiched between the two materials; and
selectively designating the bonding of the two materials as defective based on the scanned data wherein the selectively designating step includes defining an axial offset of the bonding region relative to a junction between the two materials based on the scan data and wherein the axial offset is determined based on a predefined correlation between the axial offset and width-span of the bonding point at the junction between the two materials.

24. A method for inspecting a bonding of two materials, the two materials being bonded together at a bonding point sandwiched between them, the method comprising:
using an optical coherence tomography (OCT) system, applying a sample beam through the first and a least a part of the second material and laterally scanning the sample beam across the two materials to reach and acquire scan data of the bonding point sandwiched between the two materials;
selectively designating the bonding of the two materials as defective based on the scanned data, the method further comprising,
defining a two-dimensional, cross-sectional image of the two materials based on the lateral scan across the two materials, the cross-sectional image providing a plurality of imaged lines including true boundary lines of the two materials and phantom boundary lines of the two materials, the phantom boundary lines resulting from a complex conjugate image component and being offset from the true boundary lines; and
identifying as the junction between the two materials the imaged line closest to an axial location having a predefined offset from an outer boundary of a selected one of the two materials, the predefined offset being a thickness of the selected one of the two materials.

25. A method for inspecting a bonding of two materials, the two materials being welded together at a bonding point sandwiched between them, the method comprising:
using a polarization sensitive optical coherence tomography (PS-OCT) system, the PS-OCT system measuring birefringence properties of the two materials and the bonding point before, during, and after the welding process, applying a sample beam through a first of the two materials to reach and acquire scan data of the bonding point sandwiched between the two materials; and
selectively designating the bonding of the two materials as defective based on the scanned data including measured birefringence properties.

* * * * *